US008329475B2

(12) United States Patent
Jacobs et al.

(10) Patent No.: US 8,329,475 B2
(45) Date of Patent: Dec. 11, 2012

(54) WASH PROCESS FOR REMOVING UNDESIRED COMPONENTS IN SAMPLES BEING ANALYZED

(75) Inventors: Merrit N. Jacobs, Fairport, NY (US); Ann M. Skrobach, Webster, NY (US); Andrew S. Foote, Spencerport, NY (US); Anthony C. Machulskis, Rochester, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 562 days.

(21) Appl. No.: 10/417,912

(22) Filed: Apr. 17, 2003

(65) Prior Publication Data
US 2005/0074897 A1    Apr. 7, 2005

Related U.S. Application Data

(63) Continuation-in-part of application No. 10/294,876, filed on Nov. 14, 2002, now abandoned.

(51) Int. Cl.
*G01N 33/00* (2006.01)
(52) U.S. Cl. ......... 436/177; 436/179; 436/180; 436/512
(58) Field of Classification Search .................. 436/179, 436/180, 501, 506, 512, 177
See application file for complete search history.

(56) References Cited

U.S. PATENT DOCUMENTS

| 3,279,225 A | 10/1966 | Knudson |
| 4,622,076 A | 11/1986 | Ling |
| 4,685,480 A | 8/1987 | Eck |
| 5,006,309 A | 4/1991 | Khalil |
| 5,183,638 A | 2/1993 | Wakatake |
| 5,441,895 A | 8/1995 | Jakubowicz et al. |
| 5,756,682 A * | 5/1998 | Wicks et al. ............... 530/387.9 |
| 6,013,528 A | 1/2000 | Jacobs et al. |
| 6,096,561 A * | 8/2000 | Tayi .............................. 436/518 |

(Continued)

FOREIGN PATENT DOCUMENTS
EP    213618 A2    3/1987
(Continued)

OTHER PUBLICATIONS

McNicol "Automation of Dupont's chromium dioxide magnetic particle based immunoassay" pp. 1-19, presented Apr. 13-14, 1988, in Savannah, Georgia.*

(Continued)

*Primary Examiner* — Sam P Siefke
(74) *Attorney, Agent, or Firm* — Todd J. Burns

(57) ABSTRACT

A method for removing undesired component(s) from bound desired component(s) in an analysis including: (a) providing a container having a desired component bound thereto and an undesired component; (b) dispensing wash fluid in the container at a first level sufficient to contact a portion of the bound desired component; (c) oscillating wash fluid level in the container; and (d) removing a portion of the wash fluid from the container. A method for removing undesired components from bound desired components in an analysis including steps (a) and (b) above; (c) removing the wash fluid; (d) dispensing a wash fluid at a subsequent level lower than the first level and sufficient to wash the bound desired substrate; and (e) removing wash fluid. Preferably, the desired component is an analyte being measured. Another aspect of the invention provides a method for removing an undesired component from a bound desired component in an analysis by removing a surface portion of fluid containing a portion of the undesired component.

40 Claims, 8 Drawing Sheets

U.S. PATENT DOCUMENTS

2002/0028489 A1    3/2002    Ammann et al.

FOREIGN PATENT DOCUMENTS

| EP | 213618 B1 | 3/1987 |
|---|---|---|
| EP | 330688 B1 | 6/1989 |
| EP | 533801 B1 | 3/1993 |
| EP | 0670483 | 9/1995 |
| EP | 0670483 A2 | 9/1995 |
| JP | 62-229070 | 10/1987 |
| JP | 62229070 | 10/1987 |
| JP | 89/01182 | 2/1989 |
| JP | 01202664 | 8/1989 |
| JP | 2218410 A | 8/1990 |
| JP | 06230014 | 8/1994 |
| JP | 9234437 | 9/1997 |
| JP | 11219928 | 8/1999 |
| JP | 2000-97948 | 4/2000 |
| WO | WO 87/01616 | 3/1987 |
| WO | WO 87/01616 A1 | 3/1987 |
| WO | WO 91/16979 | 11/1991 |
| WO | WO 91/16979 A2 | 11/1991 |
| WO | WO 93/20443 | 10/1993 |
| WO | WO 94/27156 | 11/1994 |

OTHER PUBLICATIONS

European Search Report, dated Dec. 21, 2005, for European Appln. No. EP 03 25 7208.

Nearac.com Search Sep. 25, 2002, Question No. 1188096.002—Oscillating Wash II.

Nearac.com Search Sep. 9, 2002, NDN 244-0187-1123-4: Optimized Sample Probe Wash on the Abbott Architect ci8200TM Analyzer to Minimize Between Sample Carryover on an Integrated Clinical Chemistry and Immunoassay Platform, Wilson, C.W. et al., Clinical Chemistry, vol. 48, No. 6 Supplement Jun. 2002, pp. A59.

U.S. Appl. 09/482,599, filed Jan. 13, 2000, Ortho-Clinical Diagnostics, Inc.

* cited by examiner

WASH PROCESS FOR REMOVING UNDESIRED COMPONENTS IN SAMPLES BEING ANALYZED

DESCRIPTION OF RELATED APPLICATIONS

This application is a continuation-in-part of U.S. application Ser. No. 10/294,876, filed Nov. 14, 2002 now abandoned, the contents of which are incorporated herein by reference in its entirety.

BACKGROUND OF THE INVENTION

1. Field of the Invention

The present invention relates to a process for removing an undesired component from a bound desired component, in particular for improving the bound-free separation efficiency. In particular, the present invention relates to a process for separating or washing a bound analyte being analyzed in an automated clinical analyzer from unbound label, particularly without decreasing processing efficiency or speed.

2. Description of the Related Art

Methods and systems for washing containers that hold samples being analyzed, such as analyzers for conducting clinical assays are known, e.g., wash stations in clinical analyzer immunochemical assay systems. For example, U.S. Pat. No. 6,096,561 and U.S. application Ser. No. 09/482,599 filed Jan. 13, 2000 entitled "Failure Detection in Automatic Clinical Analyzers" describe immunoassay analyzers that include container wash stations for washing containers containing one or more analytes bound to coated sample containers that are measured, for example, by chemiluminescence. Such systems typically contain a sample wash station that may include a wash fluid dispense nozzle and an aspirating nozzle. The sample containing analyte and reagent, e.g., label, is aspirated out of the container after it has been incubated. Wash fluid is then dispensed into and aspirated out of the container one or more times to remove any excess analyte and reagent not bound to the coating, such as streptavidin, at the side of the container. Some known surface coated containers have features, such as pockets or ledges, near the top of the container that can trap unbound material, such as unbound label, analyte, etc. These features may be the result of the process used to mold the containers and/or to keep the containers separated in a stack. See, e.g., U.S. Pat. No. 5,441,895, which describes stackable containers. The incubation, reagent metering and mixing processes involved in immunochemical assay analysis move the sample in the container in a manner that leaves a film of sample containing unbound label and/or analyte on the pockets and ledges that are in the upper regions of the container.

Typically in immunochemical assay systems, an important aspect that affects the performance is bound-free separation. The bound-free separation is controlled by two primary factors:

(1) the component or material, such as the bound label, that is intended to produce signal remains behind and intact; and (2) the unbound (i.e., free) component or material is removed as completely as possible.

In particular, there are several assays that have clinically significant performance very close to the background of the assay. This means that small amounts of unbound material present during the measurement portion of the process, particularly signal producing material, can produce a substantial adverse impact on performance.

To remove unbound material as completely as possible, a container wash process typically includes multiple wash cycles, such as filling a surface coated container to a first height on the container with a wash fluid and aspirating the wash fluid after a predetermined amount of time. For example, in one known process, a dispensing nozzle fills the container, which has a 300 µl capacity up to a height of 270 µl and then sets the soak height to 230 µl so the well can be transported during the wash incubation step (≅37-40 seconds). These steps, including the incubation step, are repeated multiple times (e.g., four times) using the same fluid heights. Unbound material that can be present in the upper regions of the container is only removed by inadvertent exposure to the wash fluid. Considerable erroneous signal can be generated when the wash fluid makes contact with unbound material in the upper regions of the container where the material is re-hydrated but not removed. The unbound material can then drop into the signal reagent during the last processing step that is intended to detect the amount of label bound to the container surface.

Another problem with known systems that remove fluid by aspiration is that the outer surface of an aspirating nozzle can become contaminated with the wash fluid containing unbound material. This can lead to contamination of the container with unbound material in subsequent wash cycles (in that particular test or across subsequent tests). Still another problem with known systems that unbound material can reside or float on top of the fluid, even after several wash steps. This can also interfere with any subsequent analysis of the desired bound material. It is believed that surfactant in wash fluid can trap unbound material enabling it to float. Upon the addition of an additional fluid, such as a signal reagent, the unbound material, can float to the surface of the fluid, where it will interfere with subsequent analysis. This may particularly be the case if the unbound material is horseradish peroxidase ("HRP"), which when bound to denatured protein may also prefer to float on the surface of the signal reagent fluid, where it will combine with the signal associated with bound HRP and create a false signal which will be read, thereby leading to erroneous results.

The problems described above may lead to the unbound material remaining in the test container and possibly interfering with the subsequent analysis of the analyte, leading to tests that need to be repeated at considerable inconvenience and expense due to inaccurate results.

It is known in the art that the unbound material in the upper regions of the container can be removed more completely if the fluid were to be filled higher in the container and remain there for the soak cycle (i.e., container wash incubation). This is not practical for a random access analyzer system since the test element needs to be transported during the soak cycle so other tests elements can be processed. Batch analyzers leave the test element static during this process step, which allows the fluid level moved to the very top of the container (positive meniscus). Even analyzers that fill the test element to the very top of the container may still have issues with not completely removing unbound label at the very top, if there are features in this region that can trap or retain unbound material. This is especially true when each wash processing cycle raises the fluid to the same height. In this process, the last processing step can cause any residual unbound material to flow into a region of the test element where it can interact with the signal generating reagents, thus producing erroneous results.

SUMMARY OF THE INVENTION

One object of the invention is to overcome the disadvantages of the known art described above. Another object of the invention is to provide an improved wash process for washing a container holding a sample being analyzed; in particular, a wash process that allows separation of undesired unbound material from desired bound material. Still another object of the invention is to provide an improved wash process for an immunochemical assay system that removes unbound material without substantially reducing the amount of signal from the bound fraction. Yet another object of the invention is to provide an improved process for analyzing an analyte having a signal strength close to the background noise. Another object of the invention is to provide for improved removal of unbound material in a time frame of ~2.5 seconds (excluding wash incubation time), which enables the test elements to be processed without any significant and preferably no degradation in the system throughput (efficiency or number or tests per hour).

The foregoing and further objects of the invention are accomplished according to one aspect of the invention that provides a method for removing an undesired component from a bound desired component in an analysis that includes the steps of: (a) providing a container having a desired component bound thereto and an undesired component; (b) dispensing a wash fluid in the container at a first level sufficient to contact at least a portion of the bound desired component; (c) oscillating the level of the wash fluid in the container; and (d) removing at least a portion of the wash fluid from the container. Another aspect of the invention provides a method for washing an analyte bound to the walls of a surface coated container of an analyzer that includes: (a) providing a surface coated container having an analyte bound thereto; (b) dispensing a wash fluid in the container at a first level sufficient to contact at least a portion of the analyte bound thereto; (c) oscillating the level of the wash fluid in the container; and (d) removing the wash fluid from the surface coated container.

Still another aspect of the invention provides a method for removing an undesired component from a bound desired component in an analysis that includes the steps of: (a) providing a container having a desired bound component bound thereto and an undesired component; (b) dispensing a wash fluid in the container at a first level sufficient to wash at least a portion of the bound desired component; (c) removing the wash fluid from the container; (d) subsequently dispensing a wash fluid in the container at a subsequent level that is lower than the first level and is sufficient to wash at least a portion of the bound desired substrate; and (e) removing the wash fluid from the container.

Yet another aspect of the invention provides a method for washing an analyte bound to the walls of a surface coated container of an analyzer that includes the steps of: (a) providing a surface coated container having an analyte bound thereto; (b) dispensing a wash fluid in the container at a first level sufficient to wash at least a portion of the analyte bound thereto; (c) removing the wash fluid from the surface coated container; (d) subsequently dispensing a wash fluid in the sample container at a second level that is lower than the first level and sufficient to wash at least a portion of the analyte bound thereto; and (e) removing the wash fluid from the sample container.

Still another aspect of the invention provides a method of determining the amount of an analyte in a sample, that includes the steps of: (a) providing a sample containing an analyte in a coated container; (b) providing a reagent in the container; (c) optionally incubating the combined sample and reagent; (d) performing a wash as described above; (e) optionally adding a signal reagent; and (f) analyzing the sample for an analyte. Preferably, the analyte being measured is Troponin I.

Another aspect of the invention provides the methods described above implemented by a computer program interfacing with a computer, and an article of manufacture that includes a computer usable medium having computer readable program code configured to conduct the methods described above.

Another aspect of the invention provides for improved removal of unbound material in a time frame of ~2.5 seconds (excluding wash incubation time), which enables the test elements to be processed without any significant and preferably no degradation in the system throughput (efficiency or number or tests per hour).

Still another aspect of the invention provides a method for removing an undesired component from a bound desired component in an analysis that includes the steps of: (a) providing a container having a desired component bound thereto and an undesired component; (b) dispensing a fluid into the container, such that at least a portion of the undesired component is on the surface of the fluid; and (c) removing a surface portion of the fluid containing the undesired portion. This aspect of the invention can be used by itself, or more preferably, can be used with the other aspects of the invention described above.

Further objects, features and advantages of the present invention will be apparent to those skilled in the art from detailed consideration of the preferred embodiments that follow.

DETAILED DESCRIPTION OF PREFERRED EMBODIMENTS

Figure 1:
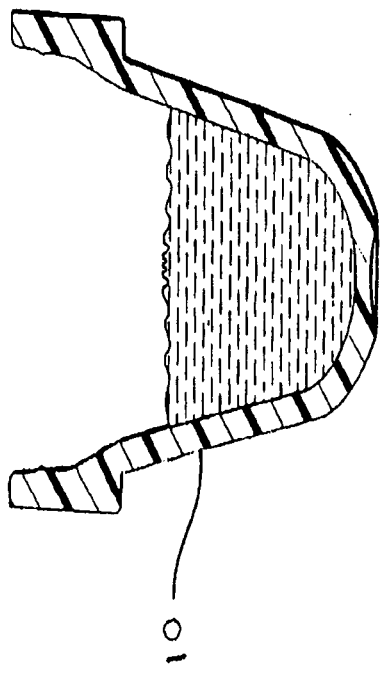
FIG. 1 shows a cup-shaped container according to one embodiment of the present invention.

The present invention provides a method for washing a container containing a sample being analyzed, in order to assure that components (such as analyte and bound label) in the sample bound to the substrate remain, while unbound components, such as unbound label, are removed from the container. While much of the foregoing and following description is related to automated immunochemical assay analyzers, the present invention is not so limited. In particular, the present process can be applied to any analysis or separation, chemical, immunological or otherwise. The coated container being washed includes those components (single or multiple) of the sample that are bound and those components (single or multiple) of the sample that need to be removed, such as excess analyte (e.g., Troponin I and HBsAg), excess reagents, such as biotin or unbound label (e.g., HRP), the liquid phase, undesired materials/interferents (e.g., hemoglobin), etc. The coated container can also include streptavidin coated containers that have not been further modified or treated, such as biotinylation. In this instance, the bound material is the streptavidin coating and the unbound material is any impurity to be removed before further treatment in the process.

According to a first preferred embodiment, a container suitable for containing a wash fluid and sample is provided. The container can include materials such as plastic, glass, metal, etc. and can be configured as a cup, well, cuvette, test tube, etc. As noted above, the container can include features from an injection molding process and/or features from stacking the containers. Prior to the wash process, the container and the sample may have been through previous processes, such as reagent addition or incubation as will be described more fully below. As used herein, a "wash cycle" is the dispensing and aspirating of wash fluid into and out of the container and does not include the incubation time, which is generally on the order of ≅37.5 seconds.

Prior to the first dispense of wash fluid, the container may have any liquid phase and/or solids not containing the portion of the sample, e.g., the analyte, not being washed, first removed, such as by aspiration. The wash fluid is then dispensed into the container. It should be understood that in some cases, it is possible for the wash fluid to be first dispensed before the sample is present in the container. However, in a preferred aspect of the invention, the sample, including the analyte and label, are present in the container prior to the first dispense. Upon dispensing, the wash fluid contacts at least a portion of the container containing the bound desired material or component to ensure removal of the undesired and unbound material or component into the wash fluid. The dispense can be accomplished with a dispensing nozzle, or any other satisfactory fluid dispensing apparatus. If a dispense nozzle is used, it can be the same or different than the aspirate nozzle, described below. In those embodiments where a pre-wash is performed before a sample is added to the container, the wash fluid may be of a different composition than the wash fluid typically used. For example, the wash fluid for a pre-wash cycle may include a protein, such as bovine serum albumin (BSA) to act as a blocking agent.

After a selected time of contact, the wash fluid is removed from the container, such as by aspirating with a nozzle, resulting in the completion of a wash cycle. Alternatively, the fluid removal can be accomplished with any other known fluid removal devices, such as inversion of the container, etc.

According to a particularly preferred embodiment, the wash cycle can include an oscillating process. Upon dispensing the wash fluid into the container, small amounts (i.e., a less than complete emptying of the container, for example,) of wash fluid are dispensed and removed from the container. The oscillating action of the wash fluid creates a moving meniscus. The moving meniscus reduces the concentration gradient at the boundary layer of the container wall by constantly refreshing the wash fluid at the surface on the container wall in contact with the moving meniscus. The meniscus moving along the surface of the container forces the wash fluid to drain from the container surface providing convective transport along the surface. That is, the moving meniscus made possible by the oscillation, enhances the fluid velocity as close as possible to the boundary layer to maximize the concentration gradient at the boundary. While moving meniscus are known to enhance diffusion at boundary layers, the present inventors believe that this is the first time such a concept has been applied to the present invention. In a preferred embodiment, two complete oscillations may be provided, one oscillation being up and down nozzle travel, or vice versa. Applicants have found that, even with the oscillation, it is possible to provide a wash cycle that takes approximately the same time as known wash processes, even though there are several additional steps that are required by the oscillation. Preferably, the wash cycle takes approximately 3 seconds, more preferably approximately 2.5 seconds.

According to another preferred aspect, after removal in the first wash cycle, a wash incubation step of approximately 37.5 seconds follows. After the wash incubation step, a further dispense and removal wash cycle may be provided. The dispense step in the further wash cycle or cycles dispenses fluid into the container at a level which is lower than a previous wash cycle. This ensures that once the upper portion of the container has been cleaned and removed of sufficient undesired material, it will no longer contact subsequent washes and not allow for the possibility of recontamination of the upper reaches of the container in subsequent wash cycles.

As many wash cycles as required can be used according to the present invention. A preferred number of wash cycles is one to six, more preferably four. Also, other steps during the wash cycle can also be performed, if desired. Moreover, the oscillating process embodiment described above can be carried out during one or all of the wash cycles.

In systems where an aspirating nozzle is used to remove the wash fluid, the rate of the nozzle descent is generally balanced with the amount of wash liquid being removed from the container. That is, the aspirating nozzle relative to the surface of the fluid will remain substantially constant. In the present invention, the inventors have found that reducing the rate of the aspirate nozzle descent and elimination of any fluid dispense during the aspirate nozzle descent, particularly in the final wash, preferably the fourth wash, reduces the likelihood that the aspirate nozzle will be submerged in the wash fluid. Submerging the nozzle in the wash fluid on the final wash cycle makes it likely that any unbound material on the outside of the nozzle will be washed off the nozzle and leave residual undesired or unbound material in the container that can give an incorrect result, such as an elevated signal. In a preferred embodiment, the rate of descent is ⅓ slower relative to the rate of descent in previous wash cycles (where the previous wash cycle rate of descent is where the fluid aspirate rate and rate of descent are balanced as described above).

Figure 2:
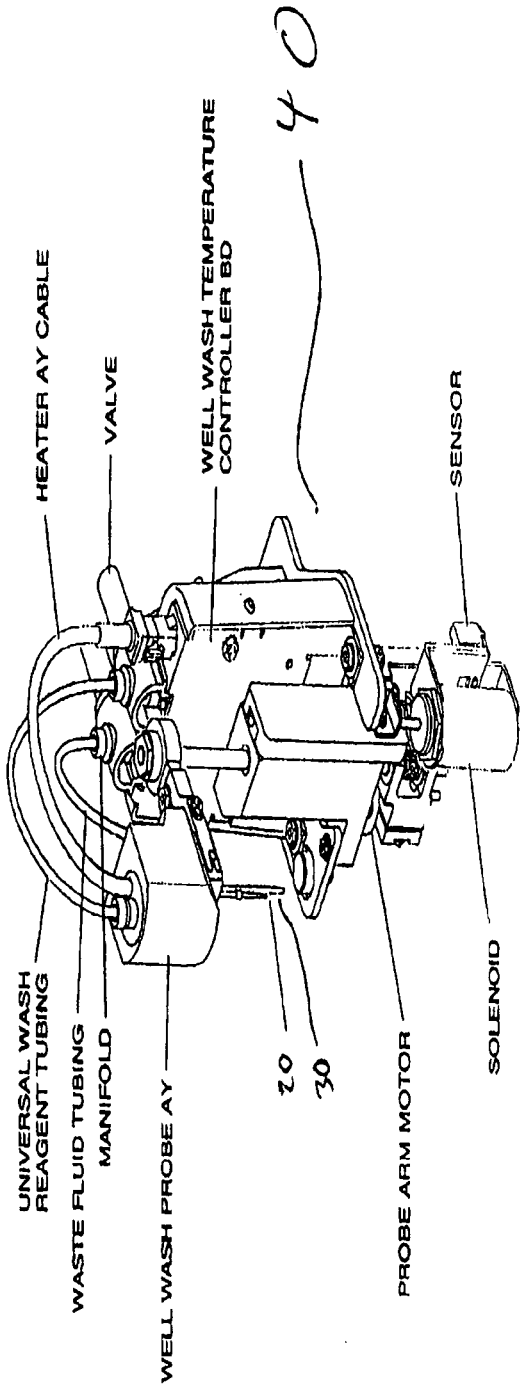
FIG. 2 shows a container wash dispenser according to one embodiment of the present invention.

In some embodiments, particularly in systems where the wash fluid is temperature controlled, the wash fluid dispense may be on during the aspirate nozzle descent. This is done to further improve the control of the wash fluid temperature during the soak cycle where the temperature control device is in the wash nozzle head 50 (FIG. 2). The nozzle contains fluid (~80 µl) that is retained by the nozzle after the temperature control element in the wash head so this amount of fluid quickly reaches room temperature. By dispensing and quickly aspirating during nozzle descent, the colder fluid in the nozzle not at wash temperature is quickly removed. In this embodiment, the present inventors have found it particularly advantageous to turn off the wash fluid dispense during the final wash aspirate nozzle descent in order to reduce the curvature of the fluid meniscus in the container. This further reduces the likelihood that the aspirate nozzle will be submerged and become contaminated.

According to another aspect of the invention, the present invention provides a method for removing an undesired component from a bound desired component by removing, preferably by aspirating, a top layer of fluid that is in the container. This aspect of the invention can be used alone, or preferably can be used with the wash process described above during any stage of the wash process before, during or after, and as shown in the description of FIGS. 6 to 9 below.

One of the problems that lead to the present invention was the problem of results that were outside the statistical norm for the sample being tested, so-called "outliers." The inventors found that one solution to outliers resided in reducing interfering undesired, generally unbound components from bound desired components using the process described in the first part of the specification. Based on the data generated in various wash processes, it was believed that another source of unbound materials was also present. This additional source of interfering unbound material is material that resides or floats on top of the fluid, even after several wash steps.

This material can also interfere with any subsequent analysis of the desired bound material. While not being bound by any theory, it is believed that surfactant in wash fluid can trap unbound material. Upon the addition of an additional fluid, such as a signal reagent, the unbound material, can float to the surface of the fluid, where it will interfere with subsequent analysis. A preferred signal incubation time is over 4 minutes. This incubation time will provide time for unbound material to become dislodged from the surfaces where it is attached and to float to the surface where it can be removed by the aspiration.

This may particularly be the case if the unbound material is label, such horseradish peroxidase ("HRP"), which is or is attached to a denatured protein. The protein may prefer to float on the surface of the signal reagent fluid, where it will combine with the signal producing reagent and create a false signal which will be read, thereby leading to erroneous results. Based on these discoveries, applicants found that removing the top layer of fluid at some point before measurement, results in fewer outliers. In the case of immunochemisty, the surface film would be removed after the addition of signal reagent. Experiments, as described in FIGS. 6 to 9 below, demonstrate that any remaining outliers were essentially eliminated or significantly reduced. This was quite unexpected and surprising because the removal of the surface layer of the fluid did not change the dose curve or degrade the precision as would normally be expected from an additional process step.

Figure 3:
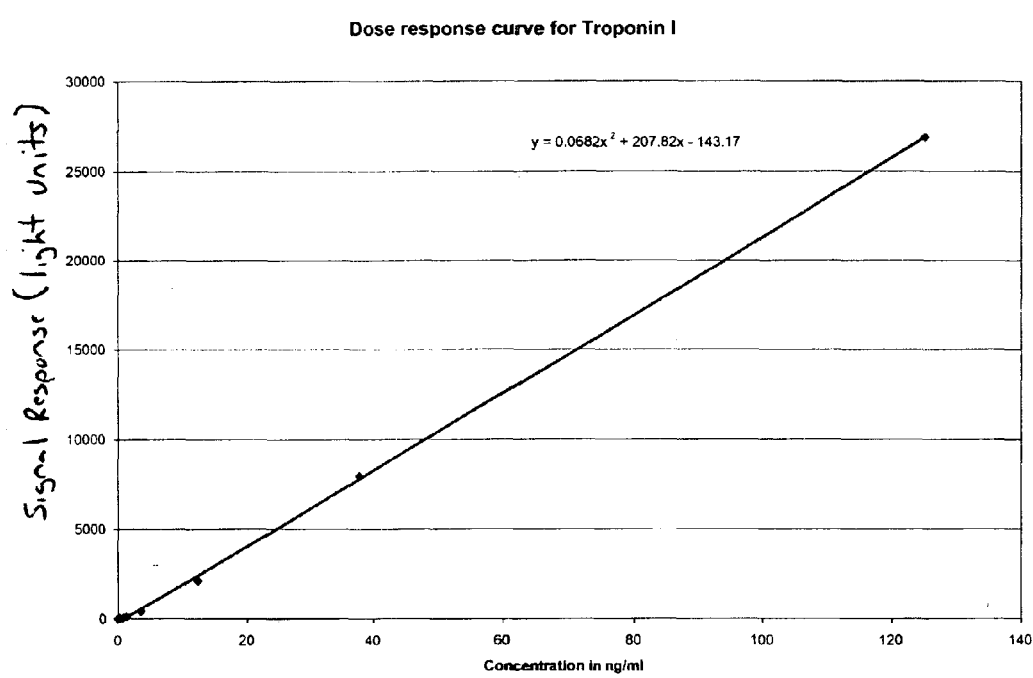
FIG. 3 shows a dose curve for Troponin I.

The dose curve is an expression describing the ratio of the signal of the assay to the amount of component that one is attempting to measure. For example, for Troponin see the data below and the plot in FIG. 3:

| Concentration (ng/mL) | Signal (light units) |
| --- | --- |
| 0 | 6.10678 |
| 0.358 | 34.3152 |
| 0.779 | 73.5325 |
| 1.22 | 120.708 |
| 3.43 | 425.336 |
| 12.3 | 2117.63 |
| 37.8 | 7953.13 |

One issue with some analytes such as Troponin in particular, is that there is very little signal in the clinically significant region from 0-0.08 ng/ml. This plot is shown in the graph of FIG. 4.

Figure 4:
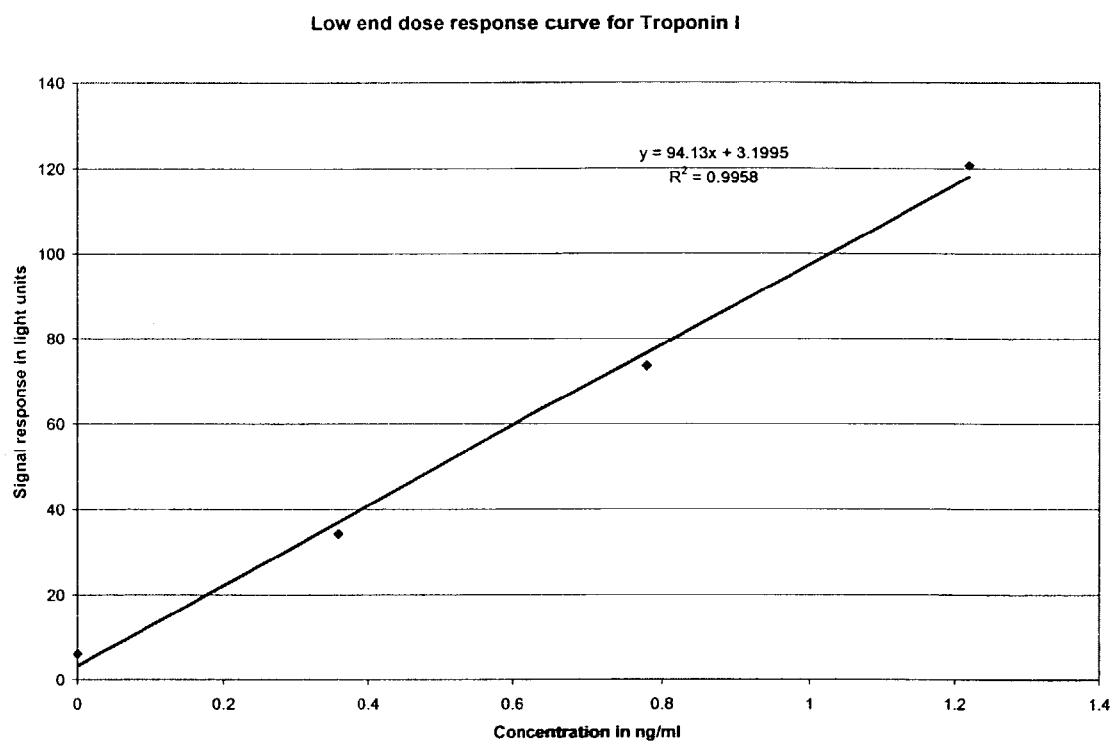
FIG. 4 shows a dose curve for Troponin I in the clinically significant region from 0-0.08 ng/ml.

As the plot in FIG. 4 demonstrates, if the line approaches horizontal one will be working with less signal and therefore have inherently more imprecision. If one were to employ a wash method that produced a more precise signal response but did this at the expense of reducing half of the usable signal in the critical range, then there would be little or no benefit unless the improvement is significantly better than 2×. An advantage of the present invention that there is a significant improvement in low end precision without reducing the amount of usable signal. This aspect of the invention is useful in any analysis that may have an interfering undersired component on the surface of the sample holder, such as a well or cuvette described above. The timing of the surface film removal depends on the system and chemistry being employed. If immunochemistry were employed, the removal would be after addition of signal reagent and any incubation. This incubation is expected to enhance the amount of material that becomes dislodged from the surface. It may also impact the amount of material that floats to the surface. It would be expected that the effectiveness of this process is greatest after some incubation period. Chemiluminescent (immunochemistry) assays will have this incubation period and not produce a buildup of signal since this type of process only produces light.

An advantage of the surface removal embodiment (hereinafter also referred to as the aspirate or aspiration embodiment) that employs an incubation of a signal producing reagent is that it enables an overall shorter time to result and better system throughput for the equivalent amount of wash efficiency. This is because the aspirate embodiment makes double use of the signal reagent incubation by turning signal reagent incubation into a supplemental wash process (soak) while incubating at the same time. For example, in a preferred embodiment described above, there is generally a total of 120 seconds of soak time between washes (3 soaks at 40 seconds each). With the preferred aspiration process, an additional soak time of 4 minutes and 40 seconds is added (i.e., the signal incubation time in certain embodiments) is provided resulting in a greater than 4 times increase for soak time. Thus, there is a longer effective wash/soak time for the embodiments that use the aspiration process compared to an equivalent method but does not employ the aspiration process.

If the analysis is a calorimetric analysis having a dye detection system, the surface film or layer should be removed before the endpoint color is measured. A dye detection system results in a buildup of color density with time if there is signal producing material present. Thus, if the aspirate embodiment is used in a calorimetric type assay the method will be somewhat modified. For example, the surface of the fluid may be aspirated multiple times during the detection incubation process. Another alternative would be to put in a wash fluid and aspirate the surface after an incubation time. An advantage of this method over the current state of the art methods having an extended wash soak time is that aspiration of the surface film before removal of the bulk fluid would be expected to remove a concentrated layer of unbound material. This unbound material could get re-deposited on the surface of the container using conventional aspiration methods where an aspiration nozzle removes the bulk fluid without first selectively removing or aspirating the surface film.

The ultimate timing of the surface film removal depends on the system and chemistry being employed and can be determined by those skilled in the art using the present specification as a guide.

In a particularly preferred embodiment, the processes described above are employed in an immunodiagnostic assay analyzer, such as those described in U.S. Pat. No. 6,069,561 and copending U.S. application Ser. No. 09/482,599 filed Jan. 13, 2000 entitled "Failure Detection in Automated Clinical Analyzers," both of which are incorporated by reference in their entireties. In preferred immunodiagnostic analyzers, the container is cup-shaped. Preferred containers are 0.35 ml, conical containers coated with a material complementary to the reagents. Container coatings can comprise materials such as streptavidin and/or other materials useful for immunochemical analysis as is well known in the art to facilitate binding by a biotinylated antigen or antibody to which an analyte binds as part of the assay chemistry. An exemplary container 10 is shown in FIG. 1. Also preferred are separate wash dispense and aspirating probes, such as the wash dispense 20 and aspiration nozzles 30 in wash unit 40 shown in FIG. 2.

In a typical immunodiagnostic analyzer, the analyzer is categorized into systems and subsystems of components that perform different processes in the sequence of measuring a sample for an analyte, such as those described in the '599 application. A typical process involves a sample being dispensed into a container that may or may not already have a reagent present in the container that is dispensed by a reagent metering system. After the reagent is added, the sample is diluted, if necessary, and then incubated. After incubation, the container is washed, in this instance according to the inventive wash. After washing, a signal reagent is added, followed by further incubation, if necessary, optionally followed by the surface removal embodiment. The signal produced by the combination bound analyte/signal reagent is read by the appropriate detector, e.g., a luminometer.

The wash process according to the present invention can be implemented by a computer program, having computer readable program code, interfacing with the computer controller of the analyzer as is known in the art.

A particularly preferred wash sequence (not including the wash incubation) is as follows (with a typical wash sequence shown for comparison).

| Wash # | Process step (known) | Known wash process | Process step (preferred embodiment) of present invention | Present invention preffered wash process |
|---|---|---|---|---|
| 1 | 1 | Turn on vacuum before starting nozzle downward travel | 1 | Starts downward travel with vacuum off |
| 1 | 2 | Starts to dispense fluid when aspirate nozzle is at the top of the incubator ring. Start of 80 μl predispense | 2 | Finds sample + reagent fluid height |
| 1 | 3 | Travels to bottom of container and waits until for 80 μl dispense to be complete | 3 | Turns on vacuum and turns on start of 80 μl predispense |
| 1 | 4 | Reverses direction with vacuum on (no delay) and starts to dispense 270 μl volume | 4 | Travels to bottom of container and waits until for 80 μl dispense to be complete |
| 1 | 5 | Waits for 270 μl of fluid to be dispense | 5 | Waits 30 ms at bottom of container with vacuum on and dispense off |
| 1 | 6 | Lowers nozzle to the 230 μl position with the vacuum on and then immediately reverses direction lifting nozzle to home with vacuum on for 800 ms to clear fluid from nozzle and line | 6 | Reverses direction with vacuum on and starts to dispense 270 μl volume waiting at the 270 μl position |
| 1 | 7 | | 7 | With dispense on and vacuum on nozzle raises to 320 μl position and waits 60 ms (sufficient time dispense of >60 μl) |
| 1 | 8 | | 8 | With dispense and vacuum on nozzle lowers to 250 μl position |
| 1 | 9 | | 9 | With dispense on and vacuum on nozzle raises to 320 μl position and waits 60 ms (sufficient time dispense of >60 μl) |

-continued

| Wash # | Process step (known) | Known wash process | Process step (preferred embodiment) of present invention | Present invention preferred wash process |
|---|---|---|---|---|
| 1 | | | 10 | Nozzle moves down to 270 μl position remains steady for 50 ms and then dispense is turned off and waits an other 30 ms |
| 1 | | | 11 | Nozzle lowers to 230 μl height with vacuum on and stays there for 30 ms before lifting (to control the fluid soak height) |
| 1 | | | 12 | Nozzle lifts to home position and incubator starts to turn with nozzle vacuum still on for 500 ms to evaluate nozzle and line of fluid |
| 2 | 1 | Turn on vacuum before starting nozzle downward travel | 1 | Starts downward travel with vacuum off |
| 2 | 2 | Starts to dispense fluid when aspirate nozzle is at the top of the incubator ring. Start of 80 μl predispense | 2 | Finds soak volume from wash #1 (should be at 230 μl) |
| 2 | 3 | Travels to bottom of container and waits until for 80 μl dispense to be complete | 3 | Turns on vacuum and turns on start of 80 μl predispense |
| 2 | 4 | Reverses direction with vacuum on (no delay) and starts to dispense 270 μl volume | 4 | Travels to bottom of container and waits until for 80 μl dispense to be complete |
| 2 | 5 | Waits for 270 μl of fluid to be dispense | 5 | Waits 30 ms at bottom of container with vacuum on and dispense off |
| 2 | 6 | Lowers nozzle to the 230 μl position with the vacuum on and then immediately reverses direction lifting nozzle to home with vacuum on for 800 ms to clear fluid from nozzle and line | 6 | Reverses direction with vacuum on and starts to dispense 270 μl volume waiting at the 270 μl position |
| 2 | 7 | | 7 | With dispense on and vacuum on nozzle raises to 320 μl position and waits 60 ms (sufficient time dispense of >60 μl) |
| 2 | 8 | | 8 | With dispense and vacuum on nozzle lowers to 250 μl position |
| 2 | 9 | | 9 | With dispense on and vacuum on nozzle raises to 320 μl position and waits 60 ms (sufficient time dispense of >60 μl) |
| 2 | 10 | | 10 | Nozzle moves down to 270 μl position remains steady for 50 ms and then dispense is turned off and waits another 30 ms |
| 2 | | | 11 | Nozzle lowers to 230 μl height with vacuum on and stays there for 30 ms before lifting (to control the fluid soak height) |
| 2 | | | 12 | Nozzle lifts to home position and incubator starts to turn with nozzle vacuum still on for 500 ms to evaluate nozzle and line of fluid |

-continued

| Wash # | Process step (known) | Known wash process | Process step (preferred embodiment) of present invention | Present invention preferred wash process |
|---|---|---|---|---|
| 3 | 1 | Turn on vacuum before starting nozzle downward travel | 1 | Starts downward travel with vacuum off |
| 3 | 2 | Starts to dispense fluid when aspirate nozzle is at the top of the incubator ring. Start of 80 µl predispense | 2 | Finds soak volume from wash #2 (should be at 230 µl) |
| 3 | 3 | Travels to bottom of container and waits until for 80 µl dispense to be complete | 3 | Turns on vacuum and turns on start of 80 µl predispense |
| 3 | 4 | Reverses direction with vacuum on (no delay) and starts to dispense 270 µl volume | 4 | Travels to bottom of container and waits for 80 µl dispense to be complete |
| 3 | 5 | Waits for 270 µl of fluid to be dispense | 5 | Waits 30 ms at bottom of container with vacuum on and dispense off |
| 3 | 6 | Lowers nozzle to the 230 µl position with the vacuum on and then immediately reverses direction lifting nozzle to home with vacuum on for 800 ms to clear fluid from nozzle and line | 6 | Reverses direction with vacuum on and starts to dispense 270 µl volume waiting at the 270 µl position |
| 3 | 7 | | 7 | With dispense off and vacuum on nozzle lowers to 220 µl position and waits 30 ms |
| 3 | 8 | | 8 | With dispense and vacuum on nozzle raises to 270 µl position waits there for the dispense to complete the 40 µl dispense (40 ms) |
| 3 | 9 | | 9 | The dispense is turned off and the nozzle lowers to 220 µl position and waits there 30 ms to control the fluid height |
| 3 | 10 | | 10 | The dispense is turned on and the nozzle raises to 250 µl position waiting for the 30 µl dispense to be completed |
| 3 | | | 11 | The dispense is turned off and the nozzle lowers to 222 µl height with vacuum on and stays there for 30 ms before lifting (which is the soak height) |
| 3 | | | 12 | Nozzle lifts to home position and incubator starts to turn with nozzle vacuum still on for 500 ms to clear nozzle and line of fluid |
| | 1 | Turn on vacuum before starting nozzle downward travel | 1 | Starts downward travel with vacuum off and finds soak height of wash #3 with level sensing |
| 4 | 2 | Starts to dispense fluid when aspirate nozzle is at the top of the incubator ring. Start of 80 µl predispense | 2 | Turn on vacuum before starting nozzle downward travel dropping at a speed that is ⅓ slower than the baseline wash rate of nozzle descent (goes to the bottom of the container). Note that there is no 80 µl dispense |

| Wash # | Process step (known) | Known wash process | Process step (preferred embodiment) of present invention | Present invention preferred wash process |
|---|---|---|---|---|
| 4 | 3 | Travels to bottom of container and waits until for 80 µl dispense to be complete | 3 | Waits at the bottom of the container for 30 ms before reversing direction |
| 4 | 4 | Reverses direction with vacuum on (no delay) and starts to dispense 270 µl volume | 4 | Turns on the dispense and lifts the nozzle to the 230 µl height waiting for 230 µl of fluid to be dispensed |
| 4 | 5 | Waits for 270 µl of fluid to be dispense | 5 | Turns off the dispense and the nozzle drops to the bottom of the container with the vacuum on at the slower rate of decline (same as the first part of wash #4) |
| 4 | 6 | Lowers nozzle to the bottom of the container with the vacuum on | 6 | The nozzle waits in the bottom of the container for 500 ms with the vacuum on (the total amount of time that the container is being evacuated is the same since the slower rate of decline took an additional 300 ms) |
| 4 | 7 | Waits at the bottom of the container for 800 ms with the vacuum on to reduce the amount of wash residual | 7 | The nozzle is lifted with the vacuum on |
| 4 | 8 | Lifts the nozzle to home with the vacuum on and leaves the vacuum on for 800 ms before the ring moves | 8 | Nozzle lifts to home position and incubator starts to turn with nozzle vacuum still on for 500 ms to clear nozzle and line of fluid |

A particularly preferred aspiration sequence is as follows (with a typical wash sequence shown for comparison).

| Process step | Process step (Known) | Process step (Preferred embodiment) of present invention | Present invention preferred aspiration process |
|---|---|---|---|
| 1 | Well with SR is below the wash nozzle at the end of the SR incubation cycle (40 seconds before read) | 1 | Well with signal reagent (SR) is below the wash nozzle at the end of the SR incubation cycle (40 seconds before read) |
| 2 | Wash nozzle is lowered with the vacuum and dispense off with the capacitance level sensing being used to trigger the stop in downward travel of the nozzle | 2 | Wash nozzle is lowered with the vacuum and dispense off with the capacitance level sensing being used to trigger the stop in downward travel of the nozzle |
| 3 | When fluid is found the nozzle stops moving down (if fluid is not found the nozzle stops at a fixed step count that is just below 175 µl height) | 3 | When fluid is found the nozzle stops moving down (if fluid is not found the nozzle stops at a fixed step count that is just below 175 µl height) |
| 4 | Nozzle immediately reverses direction if fluid is found or if the maximum travel is reached. Vacuum or dispense is never turned on | 4 | If the SR aspirate is part of the process for this well, the aspirate valve opens, the nozzle drops 5 steps and the vacuum remains on for 100 ms |
| 5 | Wash nozzle then washes the next well presented to it without a well wash prime | 5 | A total of ~25 µl of SR is removed from the well based on test data |
| 6 | If there was no well wash scheduled between successive DIVE readings of SR the wash nozzle does a well wash prime process (currently the old process) | 6 | The wash nozzle then changes direction and lifts with the vacuum on |
| 7 | | 7 | The vacuum remains on for 500 ms to dry the end of the wash probe of any residual SR and to clear to line of residual SR |

| Process step | Process step (Known) | Process step (Preferred embodiment) of present invention | Present invention preferred aspiration process |
|---|---|---|---|
| 8 | | 8 | Wash nozzle then washes the next well presented to it without a well wash prime |
| | | 9 | If there was no well wash scheduled between successive DIVE readings of SR the wash nozzle does a well wash prime process (the new probe wash process) |

The present invention has proved to be particularly useful in improving the analysis performance of Troponin I (cTnI), a protein detectable in the bloodstream 4 to 6 hours after an acute myocardial infraction. Using the above wash process (both known and the present invention), several runs were carried out to determine levels of Troponin I according to the procedure set out below.

Example 1

Figure 5:
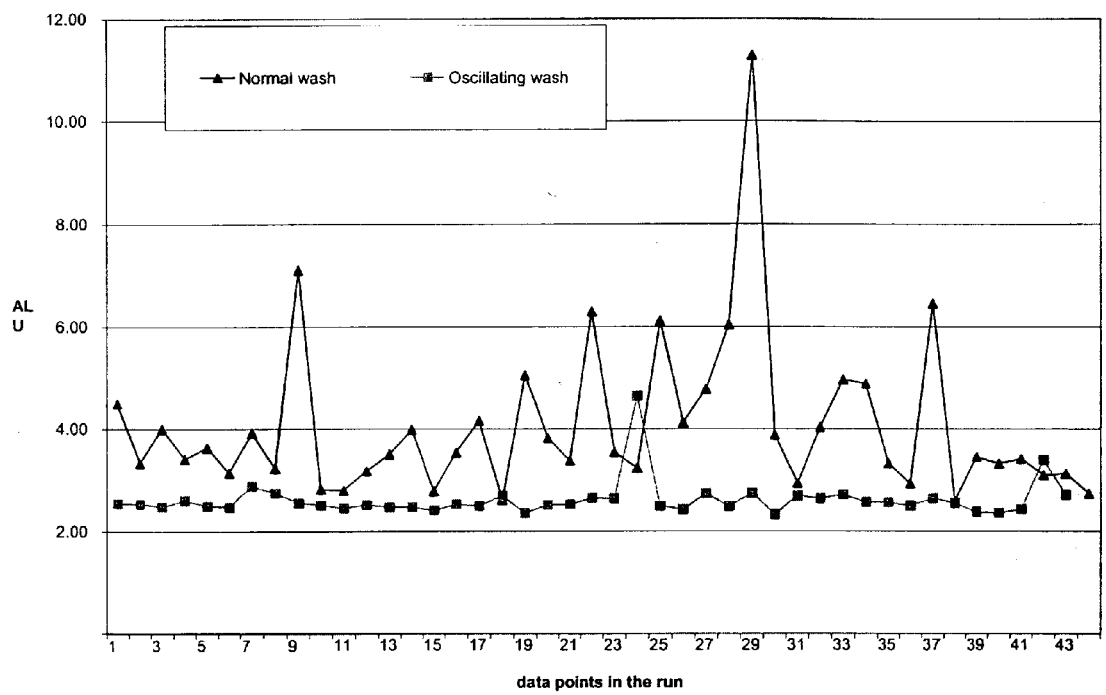
FIG. 5 shows a graph comparing assay performance for Troponin I using an oscillating wash process according to a preferred embodiment of the present invention (plotted as squares) and a conventional wash process (triangles).
Figure 6:
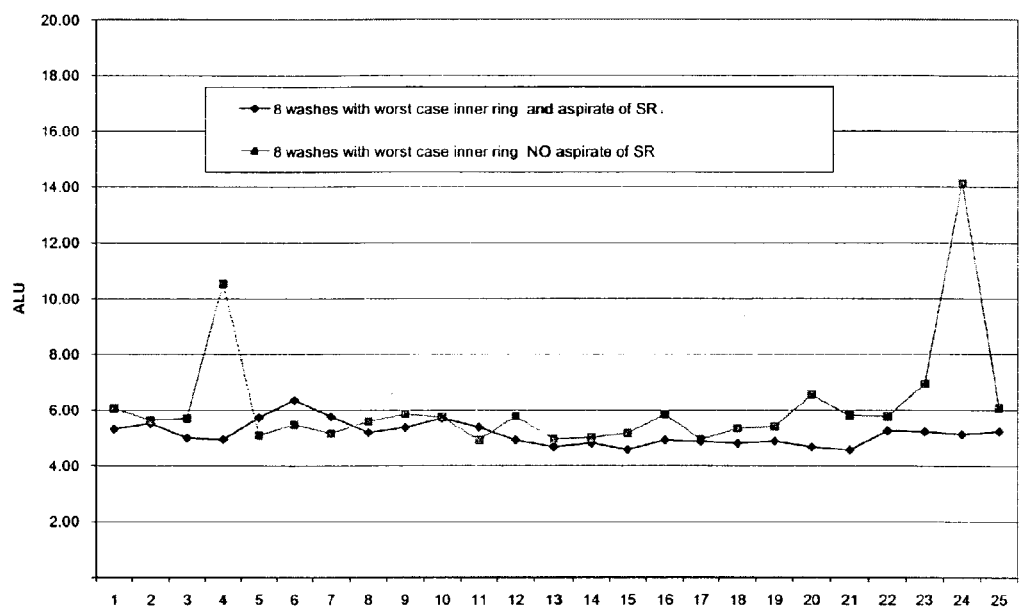
FIG. 6 shows a graph comparing assay performance for Troponin I using a wash process with signal reagent aspiration according to a preferred embodiment of the present invention (diamonds) and a conventional wash process (squares) with an analyzer deliberately configured to produce worst case performance.
Figure 7:
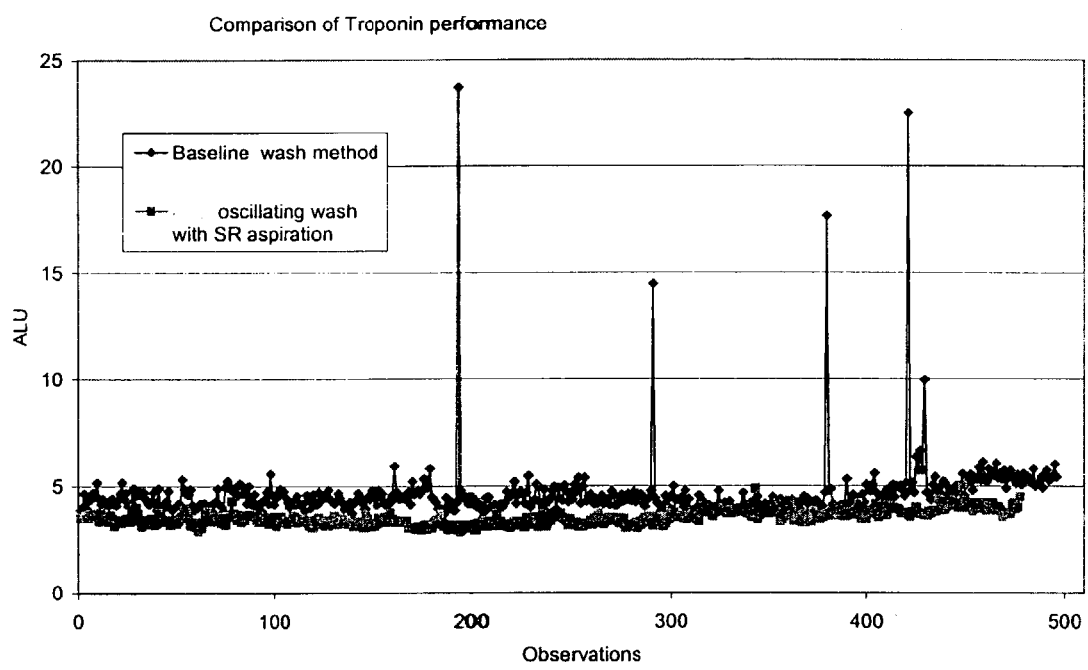
FIG. 7 shows a graph comparing assay performance for Troponin I using a wash process with both signal reagent aspiration and an oscillating wash (squares) and a conventional wash process (diamonds).

Biotin reagent was added to streptavidin-coated containers containing samples to initiate a reaction between biotinylated anti-cTnI antibody, the streptavidin coated container and the cTnI present in the sample. HRP conjugate reagent was also added to initiate a reaction between HRP-conjugated anti-cTnI antibody and the cTnI in the sample. The sample and reagent were then incubated for 8 minutes and 37° C. After incubation, the containers containing the samples were washed according to the present invention and according to the known wash process. Following washing, signal reagent containing a luminol derivative, a peracid salt and a substituted acetanilide electron transfer agent was added to produce luminescence that was read using a luminometer. The results are shown in the graph set forth in FIG. 5. As the graph shows, the results using the wash process of the present invention are much more consistent and have fewer outliers than the results using the known wash process.

Example 2

Eight washes were performed with signal reagent aspiration as described above, and eight washes without signal reagent aspiration. The results are shown in the graph set forth in FIG. 6. As the graph shows, the results using the oscillating wash process and signal reagent aspiration of the present invention are much more consistent and have fewer outliers than the results using the known wash process.

Example 3

One set of washes was performed with signal reagent aspirate and oscillating wash. Another set of washes was performed with no signal aspirate or oscillating wash. The results are shown in the graph set forth in FIG. 7. As the graph shows, the results using the wash process of the present invention are much more consistent and have fewer outliers than the results using the known wash process.

Examples 4 and 5

The present invention is also useful in improving the analysis performance of HBsAg, (hepatitis B surface antigen). Mouse monoclonal anti-HBs antibody coated containers, HRP-labeled mouse monoclonal anti-HBs antibody conjugate and HbsAg in the sample were reacted. The sample was then incubated for 29 minutes and 37° C. After incubation, the containers containing the samples were washed according to the oscillating embodiment of the present invention and according to the known wash process. Following washing, signal reagent containing a luminol derivative, a peracid salt and a substituted acetanilide electron transfer agent was added, followed by a signal reagent incubation to produce luminescence that was read using a luminometer. Prior to reading the signal, the surface film was removed using the surface removal embodiment of the invention. Using the above wash processes (both known and the present invention), several runs were carried out to determine levels of HBsAg.

Figure 8:
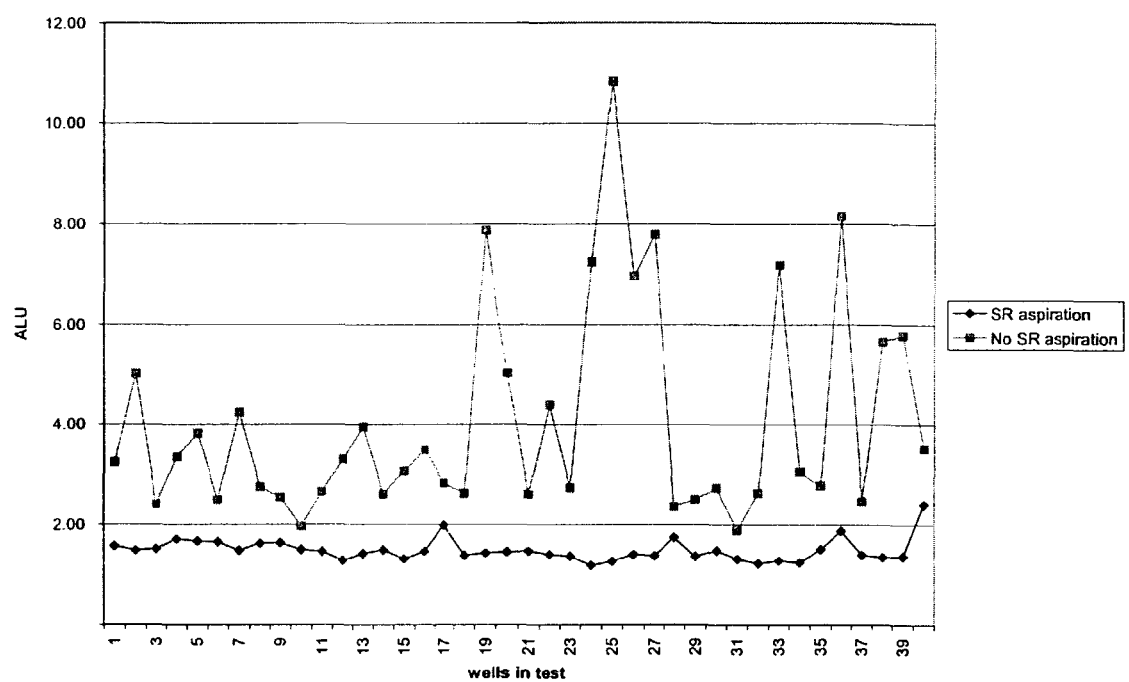
FIG. 8 shows a graph comparing assay performance for HBsAg using a wash process with both signal reagent aspiration and an oscillating wash (diamonds) and a conventional wash process (squares).
Figure 9:
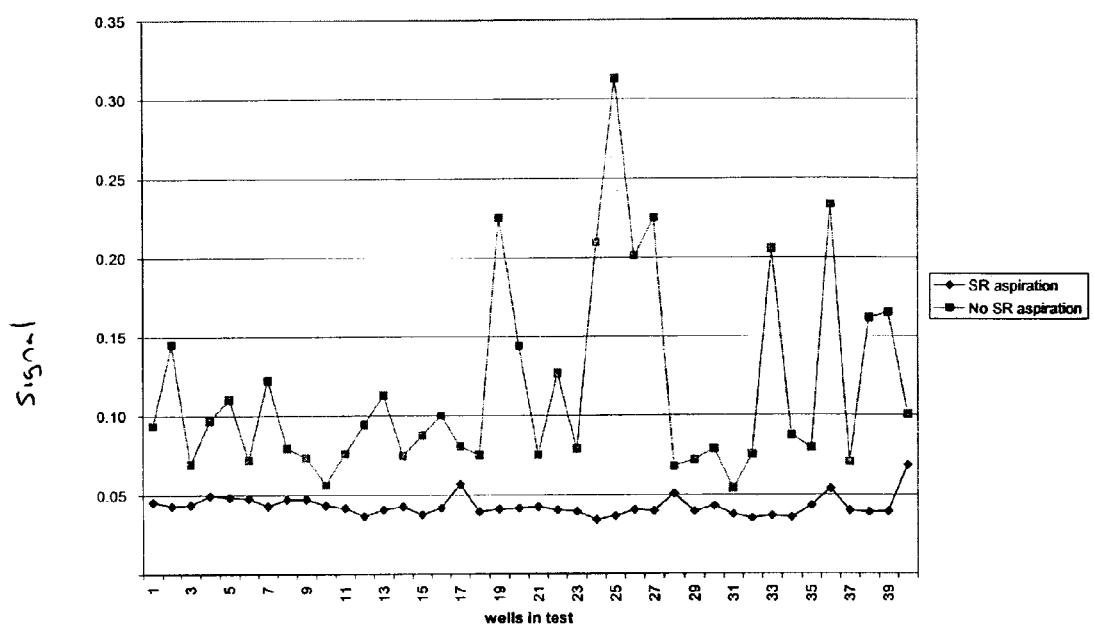
FIG. 9 shows a graph comparing assay performance for HBsAg using a wash process with both signal reagent aspiration and an oscillating wash (diamonds) and a conventional wash process (squares).

The HBsAg performance comparison is shown in FIGS. 8 and 9. Both the non signal aspiration and the signal aspiration data included wells run with and without the oscillating wash in this data set, because the data set was so small. The results demonstrate a significant difference in performance at the low end of prediction for this assay.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A method for washing an analyte and label bound to the walls of a surface coated container of an analyzer comprising:
    (a) providing a surface coated container having an analyte and label bound thereto;
    (b) dispensing a wash fluid in the container at a first level sufficient to contact at least a portion of the analyte and label bound thereto;
    (c) oscillating the level of the same wash fluid in the container to remove unbound label using either a nozzle for dispense and aspiration or separate dispense and aspiration nozzles; and
    (d) removing the wash fluid from the surface coated container.

2. A method according to claim 1, wherein steps (b)-(d) take about 2.5 seconds or less.

3. A method according to claim 1, further comprising after step (d), incubating the container containing the wash fluid.

4. A method according to claim 3, wherein the incubation takes about 37.5 seconds.

5. A method according to claim 1, wherein the container is cup-shaped with features at the upper end.

6. A method according to claim 1, wherein during the removing of the wash fluid step no additional wash fluid is dispensed and the rate of descent of the aspirating nozzle is reduced relative to a previous removing of the wash fluid to reduce or avoid the contact of the outer surface of the nozzle with the wash fluid.

7. A method according to claim 1, further comprising:
  a subsequent dispensing of a wash fluid in the container at a level that is lower than the first level and is sufficient to contact at least a portion of the bound analyte and label; and
  a subsequent removing of the wash fluid from the container, wherein the oscillating (c) occurs between any of the dispensing and removing steps.

8. A method according to claim 7, further comprising the step of adding an additional fluid after the subsequent removing of the wash fluid and removing a surface portion.

9. A method according to claim 8, wherein the additional fluid contains a signal reagent and the surface portion of the fluid is removed by aspiration before the bound analyte analyzed.

10. A method according to claim 9, wherein the analyzer is an immunodiagnostic assay analyzer and the container is cup-shaped and is coated with an antibody and the analyte being measured is Hepatitis.

11. A method according to claim 7, wherein the oscillating occurs during a dispensing and removing step subsequent to the first dispensing and removing step.

12. A method according to claim 1, wherein the analyzer is an immunodiagnostic assay analyzer.

13. A method according to claim 12, wherein the container is cup-shaped and is coated with an antibody.

14. A method according to claim 12, wherein the analyte being measured is Troponin I.

15. A method according to claim 1 implemented by a computer program interfacing with a computer.

16. A method for washing an analyte and label bound to the walls of a surface coated container of an analyzer to remove unbound label comprising:
  (a) providing a surface coated container having an analyte and label bound thereto and unbound label;
  (b) dispensing a wash fluid in the container at a first level sufficient to wash at least a portion of the analyte and label bound thereto;
  (c) removing the wash fluid from the surface coated container;
  (d) subsequently dispensing a wash fluid in the sample container at a second level that is lower than the first level and sufficient to wash at least a portion of the analyte and label bound thereto to remove unbound label;
  (e) removing the wash fluid from the sample container;
wherein the removing and dispensing of the wash fluid is performed using either a nozzle for dispense and aspiration or separate dispense and aspiration nozzles.

17. A method according to claim 16, further comprising oscillating the level of the same wash fluid between at least one of the dispensing and the removing steps.

18. A method according to claim 17, wherein the oscillating occurs during a dispensing and removing step subsequent to the first dispensing and removing step.

19. A method according to claim 16, wherein the removing the wash fluid step (e) includes aspirating the wash fluid out of the container with an aspirating nozzle.

20. A method according to claim 16, wherein the container is cup-shaped with features at the upper end.

21. A method according to claim 19, wherein during the removing of the wash fluid step (e) no additional wash fluid is dispensed and the rate of descent of the aspirating nozzle is reduced relative a previous removal of the wash fluid to reduce or avoid the contact of the outer surface of the nozzle with the wash fluid.

22. A method according to claim 16, wherein the dispensing and removing the wash fluid steps occurs at least four times, with the subsequent wash fluid levels lower than or equal to previous levels and at least one subsequent level lower than a previous level.

23. A method according to claim 16, wherein the analyzer is an immunodiagnostic assay analyzer.

24. A method according to claim 23, wherein the container is cup-shaped and is coated with an antibody.

25. A method according to claim 23, wherein the container is cup-shaped and is coated with an antibody.

26. A method according to claim 23, wherein the analyte being measured is Troponin I.

27. A method according to claim 16, wherein the removing the wash fluid steps includes aspirating the wash fluid out of the container with an aspirating nozzle.

28. A method according to claim 22, wherein the removing the wash fluid steps includes aspirating the wash fluid out of the container with an aspirating nozzle.

29. A method according to claim 28, wherein during the fourth removal of the wash fluid, no additional wash relative to an earlier removal of the wash fluid is dispensed and the rate of descent of the aspirating nozzle is reduced relative to an earlier removal of the wash fluid to reduce or avoid the contact of the outer surface of the nozzle with the wash fluid.

30. A method of determining the amount of an analyte in a sample, comprising the steps of:
  (a) providing a sample containing an analyte in a coated container;
  (b) providing a reagent in the container;
  (c) optionally incubating the combined sample and reagent;
  (d) performing the wash according to claim 1;
  (e) optionally adding a signal reagent; and
  (f) analyzing the sample for an analyte.

31. A method of determining the amount of an analyte in a sample according to claim 30, wherein a fluid containing a signal reagent is added in step (e) and further comprising (e1) removing the surface of the signal reagent fluid.

32. A method of determining the amount of an analyte in a sample according to claim 31, wherein the step of removal (e1) is by aspiration.

33. A method of determining the amount of an analyte in a sample, comprising the steps of:
  (g) providing a sample containing an analyte in a coated container;
  (h) providing a reagent in the container;
  (i) optionally incubating the combined sample and reagent;
  (j) performing the wash according to claim 16;
  (k) optionally adding a signal reagent; and
  (l) analyzing the sample for an analyte.

34. A method of determining the amount of an analyte in a sample according to claim 33, wherein a fluid containing a signal reagent is added in step (k) and further comprising (k1) removing the surface of the signal reagent fluid.

35. A method of determining the amount of an analyte in a sample according to claim 34, wherein the step of removal (k1) is by aspiration.

36. A method for removing unbound label from a bound analyte and bound label in an analysis comprising the steps of:
  (a) providing a container having an analyte and label bound thereto and unbound label;
  (b) dispensing a signal reagent into the container, such that at least a portion of the undesired component is on the surface of the signal reagent; and (c) removing a surface portion of the signal reagent containing the undesired portion.

37. A method according to claim 36, further comprising (d) analyzing the analyte.

38. A method according to claim 36, wherein surface portion of the fluid is removed by aspiration.

39. A method according to claim 37, wherein the analysis is conducted in an immunodiagnostic assay analyzer and the container is cup-shaped and is coated with an antibody and the analyte being measured is Hepatitis.

40. A method according to claim 37, wherein there is a longer effective wash/soak time compared to a method that does not employ the surface removal step.

\* \* \* \* \*